(12) United States Patent
Brown et al.

(10) Patent No.: US 7,169,858 B2
(45) Date of Patent: Jan. 30, 2007

(54) POLYFLUORINATED COMPOUNDS USEFUL AS SURFACTANTS, FOAM CONTROL AGENTS AND/OR RHEOLOGY MODIFIERS

(75) Inventors: David W. Brown, Ambler, PA (US); Kenneth Breindel, Lansdale, PA (US); Ronald W. Broadbent, Horsham, PA (US); Michael S. Wiggins, Lansdale, PA (US)

(73) Assignee: Cognis Corporation, Cincinnati, OH (US)

( * ) Notice: Subject to any disclaimer, the term of this patent is extended or adjusted under 35 U.S.C. 154(b) by 301 days.

(21) Appl. No.: 10/788,136

(22) Filed: Feb. 26, 2004

(65) Prior Publication Data

US 2004/0219350 A1 Nov. 4, 2004

Related U.S. Application Data

(60) Provisional application No. 60/450,416, filed on Feb. 27, 2003.

(51) Int. Cl.
*C08G 65/22* (2006.01)
*C08G 65/24* (2006.01)

(52) U.S. Cl. .................... 525/403; 528/421
(58) Field of Classification Search ........... None
See application file for complete search history.

(56) References Cited

U.S. PATENT DOCUMENTS

| 4,113,748 | A | * | 9/1978 | Hager et al. ............. 549/556 |
| 4,310,698 | A | * | 1/1982 | Cooke ..................... 568/46 |
| 4,766,234 | A | * | 8/1988 | Wehowsky et al. ........ 560/26 |
| 5,827,453 | A |   | 10/1998 | Gross et al. ............. 252/321 |
| 5,877,245 | A |   | 3/1999 | Wiggins et al. .......... 524/366 |
| 6,465,605 | B2 |  | 10/2002 | Breindel et al. ......... 528/403 |

FOREIGN PATENT DOCUMENTS

| EP | 240601 A | * | 10/1987 |
| JP | 04036274 A | * | 2/1992 |
| SU | 1779010 A1 | * | 5/1995 |

* cited by examiner

Primary Examiner—Robert Sellers
(74) Attorney, Agent, or Firm—John F. Daniels

(57) ABSTRACT

Reaction products prepared by processes which comprise reacting:
A) at least one compound having the general formula I:

$$R^1(X)_3 \quad (I)$$

wherein each X group independently represents a halogen atom or one X group represents a halogen atom and two X groups represent an epoxy oxygen atom, which is attached to two adjacent carbon atoms in the $R^1$ group to form an epoxy group, and $R^1$ is an alkanetriyl group having from 3 to 10 carbon atoms; and
B) at least one compound having the general formula II $$R^2X(AO)_nY \quad (II)$$

wherein $R^2$ represents a polyfluorinated organic group having from 1 to 36 carbon atoms and at least two fluorine atoms; X represents —O—, —S—, or $NR^3$— where $R^3$ is hydrogen or a $C_1$–$C_{18}$ alkyl group; each AO group is independently an ethyleneoxy, 1,2-propyleneoxy, or 1,2-butyleneoxy group, n is a number of from 0 to 200; and Y represents hydrogen, a mercapto group, an amino group or a $C_1$–$C_6$ alkylamino group in place of a terminal —OH group, with the proviso that when Y is a mercapto, amino, or a $C_1$–$C_6$ alkylamino group, n is at least 1; are described.

19 Claims, No Drawings

POLYFLUORINATED COMPOUNDS USEFUL AS SURFACTANTS, FOAM CONTROL AGENTS AND/OR RHEOLOGY MODIFIERS

CROSS-REFERENCE TO RELATED APPLICATIONS

This application claims priority, under 35 U.S.C. §119(e), of U.S. Provisional Patent Application No. 60/450,416, filed on Feb. 27, 2003, the entire contents of which are hereby incorporated by reference.

BACKGROUND OF THE INVENTION

Surface active foam control agents and detergency enhancement agents are widely used in both aqueous and nonaqueous compositions. However, these agents vary in their effectiveness, and new and more effective agents are in constant demand.

BRIEF SUMMARY OF THE INVENTION

The present invention relates to compounds useful as surfactants, and/or foam control agents, and/or rheology modifiers.

One embodiment of the present invention includes polyfluorinated reaction products prepared by a process comprising reacting:

A) at least one compound of formula I:

$$R^1(X)_3 \qquad (I)$$

wherein each X group is a halogen atom or one X group is a halogen atom and two X groups represent an epoxy oxygen atom, which Is attached to two adjacent carbon atoms in the $R^1$ group to form an epoxy group, and $R^1$ is an alkanetriyl group containing from 3 to 10 carbon atoms; and B) at least one compound having the formula II:

$$R^2X(AO)_nY \qquad (II)$$

wherein $R^2$ is a polyfluorinated aliphatic or aromatic organic group having from 1 to 36 carbon atoms and at least two fluorine atoms, preferably at least 3 fluorine atoms, attached to carbon atoms in the hydrocarbon group in place of hydrogen atoms; X is —O—, —S—, or $NR^3$— where $R^3$ is hydrogen or a $C_1$–$C_{18}$ alkyl group; each AO group is independently an ethyleneoxy, 1,2-propyleneoxy or 1,2-butyleneoxy group, n is a number of from 0 to 200, preferably from 1 to 100, more preferably from 2 to 20; and Y is hydrogen, or Y can be a mercapto group or an amino group (amino or $C_1$–$C_8$ alkylamino group) in place of a terminal —OH group, provided that when Y is mercapto, amino, or a $C_1$–$C_6$ alkylamino group, n is at least 1.

In the above reaction products, the mole ratio of the linking compound A) to B) is from 0.1:1 to 5:1, preferably from 0.6:1 to 2:1, more preferably from 0.8:1 to 2:1 and most preferably from 1.0:1 to 1.5:1.

In another embodiment of the present invention, polyfluorinated reaction products are prepared by a process comprising reacting: A) at least one compound of formula I; B) at least one compound having the formula II; and C) at least one compound selected from the group consisting of polyols and compounds of the general formula (III):

$$HO—(AO)_z—H \qquad (III)$$

wherein each AO independently represents an alkoxide selected from the group consisting of ethyleneoxy, 1,2-propyleneoxy, or 1,2-butyleneoxy; and z represents a number of from 1 to 500. Certain preferred compounds suitable for use as component C) include diethylene glycol, triethylene glycol and hexamethylenediol. In those embodiments wherein the process further comprises reacting a component C) with component A) and component B), the ratio of moles of component A) to the sum of the OH equivalents (or other reactive hydrogen species, i.e., —SH, —NH) in components B) plus C) is from 0.7:1 to 0.99:1, and preferably from 0.7:1 to 0.9:1, and more preferably from 0.8:1 to 0.9:1.

Yet another embodiment of the present invention includes compositions comprising a compound of the general formula (IV):

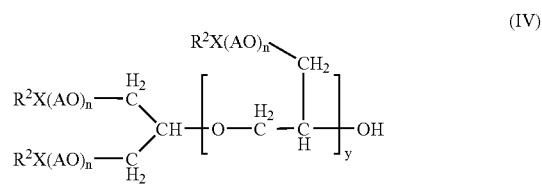

wherein each $R^2$ independently represents a polyfluorinated aliphatic or aromatic organic group having from 1 to 36 carbon atoms and at least two fluorine atoms; each X is independently an —O—, —S—, or $NR^3$— where $R^3$ is hydrogen or a $C_1$–$C_{18}$ alkyl group; each AO independently represents an alkoxy group selected from the group consisting of ethyleneoxy, 1,2-propyleneoxy and 1,2-butyleneoxy; each n independently represents a number of from 0 to 200; and y represents a number of from 0 to 12.

The above reaction products are useful as surfactants, and/or foam control agents, and/or rheology modifying agents in aqueous and nonaqueous compositions. The surfactant, foam control, and/or rheology modifying quantities of the reaction products of the invention are usually in the range of from 0.001 to 5% by weight, preferably from 0.1 to 3% by weight, based on the weight of the aqueous or nonaqueous composition. The present invention includes such aqueous and nonaqueous compositions, and also relates to processes for preparing the above reaction products and to methods for their use.

DETAILED DESCRIPTION OF THE INVENTION

Other than in the operating examples, or where otherwise indicated, all numbers expressing quantities of ingredients or reaction conditions used herein are to be understood as modified in all instances by the term "about".

In the above compounds of component A), the linking compound of formula I is preferably epichlorohydrin or another epihalohydrin. Also, trihaloalkanes can be used, such as 1,2,3-trichloropropane, 1,2,4-trichlorobutane, 1,3,6-trichlorohexane, and the like. Instead of chlorine in the epihalohydrins and the trihaloalkanes, the corresponding bromine and iodine compounds can also be used, including compounds containing two or even all three of the above halogens.

The component B) compounds of formula II are polyfluorinated organic (optionally alkoxylated) alcohols or the corresponding sulfhydryl or amine compounds.

The $R^2$ group in reactant B) and in the compounds of formula (IV) can be a polyfluorinated branched or unbranched alkyl group containing at least 2 fluorine atoms up to alkyl groups in which all hydrogen groups are substituted with fluorine atoms. Alkyl groups of this type preferably have from 1 to 22 carbon atoms, more preferably from 1 to 12 carbon atoms, and most preferably from 1 to 3 carbon atoms. Examples of polyfluorinated alkyl groups include but are not limited to di- and tri-fluoromethyl, ethyl containing from 2 to 5 fluorine atoms, isopropyl containing from 2 to 7 fluorine atoms, and 12-trifluorododecyl.

The $R^2$ group can also be a polyfluorinated saturated carbocyclic group, e.g. a $C_5$ or $C_6$ carbocyclic group containing at least 2 fluorine atoms, or a saturated heterocyclic group containing at least 2 fluorine atoms attached to carbon atoms.

When the $R^2$ group is a fluorinated aromatic hydrocarbon group, the group is preferably a phenyl group containing from 2 to 5 fluorine atoms or a tolyl group containing from 2 to 7 fluorine atoms, or a xylyl group containing from 2 to 9 fluorine atoms.

The aromatic hydrocarbon group can also be a fluorinated arenyl group having from 7 to 36 carbon atoms, preferably a fluorinated benzyl group containing from 2 to 7 fluorine atoms.

Preferred $R^2$ groups are $C_1$–$C_3$ alkyl groups in which all available hydrogen atoms attached to carbon atoms are substituted with fluorine atoms.

When an X group in formula II or in the compounds of formula (IV) is an —S—group, the $R^2$ group will preferably have from about 1 to about 12 carbon atoms, more preferably from 1 to 3 carbon atoms, examples of which include but are not limited to, trifluoromethyl mercapto, polyfluorinated dodecyl mercapto and polyfluorinated 1-hexadecanethio.

When an $R^2X$-group of formula II or the compounds of formula (IV) is a secondary or tertiary amino group, the group preferably contains from 1 to 12 carbon atoms, more preferably from 1 to 3 carbon atoms, and n is preferably a number of from 1 to 50. Examples of primary and secondary amines useful for obtaining the $R^2X$-group include, but are not limited to, methyl amine, ethyl amine, isopropyl amine, dibutyl amine, cyclohexyl amine, isodecyl amine, and dioctylamine wherein the alkyl and cycloalkyl groups contain a total of at least 2 fluorine atoms.

When X and/or Y in formula II, or the X group in a compound of formula (IV) is an amine or sulfhydryl group, the resulting compounds can be readily prepared from the corresponding polyfluoro alcohols wherein the terminal hydroxy group is replaced by an —SH group or by an amine nitrogen. For example, a compound of formula II where Y is —OH can be subjected to a catalyzed ammoniation (with ammonia, or a lower alkylamine) for replacement of the hydroxyl or catalytically with hydrogen sulfide.

In the compounds of formula II and the compounds of formula (IV), the AO groups when present are preferably all ethyleneoxy groups. However, as stated above, each AO group can be independently an ethyleneoxy (EO), 1,2-propyleneoxy (PO), or 1,2-butyleneoxy (BO) group, i.e. any one or more of such groups can be present, and they can be present in any order, as well as be present in blocks, e.g. compounds of formula II(a):

(IIa)

wherein $R^2$ has the meaning given above, m is a number of from 0 to 100, preferably from 1 to 50, p is a number of from 0 to 50, e.g. from 1 to 50, and q is a number of from 0 to 50, e.g. from 1 to 50. Compounds of formula II(a) in which $R^2$ is a branched chain alkyl group having from 1 to 12 carbon atoms, preferably from 1 to 3 carbon atoms, m is a number of from 2 to 20, and p and q are 0 are preferred.

The degree of hydrophilic and hydrophobic properties of the reaction products of components A) and B) can be readily controlled by controlling the type and number of alkyleneoxy groups in component B). For example, the greater the number of ethyleneoxy groups present, the greater the water solubility, while the presence of 1,2-propyleneoxy groups and/or 1,2-butyleneoxy groups for example, will decrease water solubility.

In general, the compounds of formula II(a) wherein the sum of m, p, and q, is at least 1, and especially at least 2 are preferred for use herein.

The compounds of component C) can be polyols, including diols, triols and higher hydroxy-functionality polyols, as well as polyalkylene glycols of the formula (III) in which the AO groups are as defined above for the compounds of formula II. The AO groups are preferably all ethyleneoxy groups. The value for z in formula III is preferably a number from 50 to 500. Certain preferred compounds suitable for use as component C) include diethylene glycol, triethylene glycol and hexamethylenediol.

The above reaction products can be prepared by the processes disclosed in U.S. Pat. No. 5,827,453, U.S. Pat. No. 5,877,245 and/or U.S. Pat. No. 6,465,605, the entire disclosure of each being expressly incorporated herein by reference.

In general, the component A) and B) reactants are reacted together, preferably in the presence of an inert organic solvent such as toluene that will azeotrope water, and in the presence of a base, such as aqueous sodium hydroxide, at a temperature of from 60° to 125° C. Preferably component B) is first mixed with the base and the organic solvent, and water is removed by azeotropic distillation. Then component A) is slowly added and the reaction continued until the reaction is completed. The reaction mixture is filtered and vacuum stripped to remove the organic solvent.

In certain preferred embodiments of the present invention, the compounds of the general formula (IV) include those wherein each $R^2$ represents a linear or branched aliphatic or aromatic polyfluorinated hydrocarbon group having from 1 to 12 carbon atoms; wherein each X represents an oxygen atom; each n represents a number of from 1 to 100; and y represents a number of from 0 to 12. In certain more preferred embodiments of the present invention, the compounds of the general formula (IV) include those wherein each AO represents ethyleneoxy. In some preferred embodiments, each n represents a number of from 1 to 10. In certain more preferred embodiments, the compounds of the general formula (IV) include those wherein each $R^2$ represents a linear or branched aliphatic or aromatic polyfluorinated hydrocarbon group having from 1 to 12 carbon atoms; wherein each X represents an oxygen atom; each AO represents ethyleneoxy; each n represents a number of from 1 to 10; and y represents a number of from 0 to 12. Certain preferred embodiments include compounds of the general formula (IV) wherein y represents a number of from 1 to 12. Other preferred embodiments include compounds of the general formula (IV) wherein y represents a number of from 1 to 6. Other preferred embodiments include compounds of the general formula (IV) wherein y represents a number of from 6 to 12.

The reaction products and compounds of formula (IV) according to the various embodiments of the present invention can be readily formulated to be soluble in aqueous compositions and/or nonaqueous compositions, depending, as discussed above, on the quantity of ethylene oxide, propylene oxide, and butylene oxide present in the reaction product, as well as the number of carbon atoms and fluorine atoms in the $R^2$ group.

Examples of compositions containing the reaction products and compounds of formula (IV) according to the various embodiments of the present invention include all aqueous and nonaqueous compositions that require, or can benefit from, the presence of a defoaming or antifoaming agent, a low foaming surfactant, and/or a rheology-modifying agent.

The reaction products and compounds of formula (IV) according to the various embodiments of the present invention used in the compositions of the present invention are effective defoamers and antifoaming agents in both aqueous and nonaqueous compositions, having rapid foam knockdown, persistent effects, good shelf life, absence of adverse effects on the compositions, ease of handling, low toxicity to manufacturing personnel and users, very good cost-effectiveness, very good chemical stability in both acidic and basic compositions, and good heat stability.

Examples of such compositions of the invention which are usually liquid at ambient temperatures, include, but are not limited to, the following:

1. Water-based and solvent based paints. Solvent-based paints and water-based paints are usually made up of four basic groups of chemical raw material: binders or resins, pigments, solvents, and additives. The term "solvents" means water in water-based paints and nonaqueous solvents, which are usually hydrocarbon solvents, in solvent based paints. When a paint is applied to a surface, the water or organic solvents begin to evaporate while the binder, pigments, and additives remain on the surface to form a hard dry solid film. The paint formulator selects the proper type and concentration of raw material from each of these groups that will provide paint with the desired end use properties.

2. Natural and synthetic latex and other polymer-containing compositions in addition to latex paints.

3. Aqueous and nonaqueous adhesive compositions. Such adhesive compositions comprise a resin system, e.g. epoxy resins, phenolic resins, acrylic monomers and resins, urethanes, and the like. Elastomeric polymers are present in pressure-sensitive adhesives and in solvent-based adhesives. Emulsion-based adhesives are polymer-based, e.g. poly (vinyl acetate)—poly (vinyl alcohol) copolymers.

4. Enamels, which are types of oil-base paints containing binders that form a film by oxidation or polymerization on exposure to air and which have an outstanding ability to form an especially smooth film. Enamels are usually intended for use as top coats and contain relatively less pigment than paint formulations for priming and surfacing. Enamels consist of an intimate dispersion of pigments in a varnish or resin vehicle. The vehicle may be an oil-resin mix or entirely synthetic resin. Those containing drying oils are converted to films by oxidation; those comprised wholly of synthetic resins may be converted by either heat or oxidation, or both.

5. Lacquers, which are protective or decorative coatings that dry primarily by evaporation of solvent, rather than by oxidation or polymerization. Lacquers were originally comprised of high-viscosity nitrocellulose, a plasticizer (dibutyl phthalate or brown caster oil), and a solvent. Later, low viscosity nitrocellulose became available; this was frequently modified with resins such as ester gum or rosin. The solvents used are ethanol, toluene, xylene, and butyl acetate. Together with nitrocellulose, alkyd resins are used to improve durability. The nitrocellulose used for lacquers has a nitrogen content of 11–13.5% and is available in a wide range of viscosities, compatibilities, and solvencies. Chief uses of nitrocellulose-alkyd lacquers are for coatings for metal as well as other products. Various types of modified cellulose are also used as lacquer bases, combined with resins and plasticizers. Many noncellulosic materials, such as dibutyl phthalate, butylbenzyl phthalate, vinyl and acrylic resins are also used, as are bitumens, with or without drying oils, resins, etc.

6. Baking finishes, which are paints or varnishes that require baking at temperatures greater than 66° C. for the development of desired properties. Such finishes are based on oil-modified alkyd, melamine, epoxy, e.g. epoxy esters, nitrocellulose, or urea resins, or combinations of these. Baking is often done by infrared radiation producing high molecular weight coatings that are dense and tough.

7. Other solvent-borne coating compositions contain resins such as alkyds (polyester resins made from polybasic acids and polyhydric alcohols), epoxides, polyurethanes, polyesters other than alkyds, and amino crosslinkers which are modified melamines.

8. Thermosetting acrylic resin based coatings. The acrylic resins are mono- or copolymers of acrylic acid or methacrylic acid esters. Some of the common monomers are methyl methacrylate, butyl methacrylate, methyl acrylate, butyl acrylate, ethyl acrylate, and 2-ethylhexyl acrylate. Thermosetting acrylic resins have at least one monomer belonging to the acrylic family which will react with itself or other resins at elevated temperatures to crosslink in order to cure. In addition to acrylate monomers previously mentioned, acrylonitrile, acrylamide, styrene, and vinyl toluene are often used in these polymers. Polymers which react to crosslink primarily because of hydroxyl groups are usually combined with an amine resin. Thermosetting acrylic paints are hard and stain-resistant and have high gloss.

9. Phenolic coatings, which contain phenolic resins are used in coatings are primarily made from phenol and parasubstituted phenols reacted with formaldehyde to form methylol groups on the phenol ring. Condensation polymers are then produced by reacting these groups with phenol. Phenolic coatings are fast drying and have high build and good resistance to moisture and chemicals. Oil-modified phenolaldehyde finishes are sometimes used for aluminum paints.

10. Polyurethane coatings are based upon reactions of isocyanates. Urethane coatings have excellent solvent and chemical resistance, abrasion resistance, hardness, flexibility, gloss, and electrical properties.

11. Organic finish removers, including paint removers, are usually methylene chloride-containing compositions. The low molar volume of methylene chloride allows it to rapidly penetrate the finish by entering the microvoids of the finish. When the solvent reaches the substrate, the remover releases the adhesive bond between the finish and the substrate and causes the finish to swell. The result is a blistering effect and an efficient rapid lifting action. Larger molecule solvents generally cannot cause this lifting action and must dissolve the finish. When methylene chloride is used in amounts of 78% or more, even with flammable cosolvents, the mixture is nonflammable. A typical methylene chloride base remover includes cosolvents, activators, evaporation retarders, corrosion inhibitors, thickeners, and wetting agents. Typical cosolvents include methanol, ethanol, isopropyl alcohol, or toluene. The selection of cosolvents depends on the requirement of the formula and their interaction with other ingredients. Methanol is a common cosolvent in methylene chloride formulas since it has good solvency and is needed to swell cellulose-type thickening agents. Other paint and finish removers include petroleum solvent-based composition such as mineral spirits; blends of acetates and alcohols; and acetone-based, methyl ethyl ketone-based, or toluene-based finish removers.

12. Drying oils, which are synthetic or natural oils that oxidize upon exposure to air from a liquid film to a solid, dry film. Most natural drying oils are derived from plant seeds, e.g. linseed oil which is obtained from flaxseed, soybean oil, perilla, safflower, sunflower, walnut oil, tung oil, oiticica oil, dehydrated castor oil, tall oil, marine fish oils, and the like.

13. Varnishes, which are solutions of drying oils containing dissolved solid resins, followed by dilution with a hydrocarbon solvent.

The present invention will now be illustrated in more detail by reference to the following specific, non-limiting examples.

EXAMPLE 1

Preparation of the Reaction Product of trifluoromethyl alcohol•4EO and epichlorohydrin:

About 117 grams of trifluoromethyl alcohol ethoxylated with an average of 4 moles of ethylene oxide (0.45 OH equivalents) is mixed with 385 grams of toluene and 54 grams of 50% aq. NaOH (0.675 equivalents). The water is removed by azeotropic distillation and when a moisture level of less than 0.8% is reached, about 46 grams (0.51 equivalents) of epichlorohydrin are slowly added. This mixture is allowed to react at 100°–110° C. for 24 hours. This mixture is removed and filtered to remove the NaCl and vacuum stripped to remove the toluene to give a liquid reaction product.

EXAMPLE 2

Preparation of the Reaction Product of 10,10-difluorodecyl alcohol•4EO and epichlorohydrin:

About 166 grams of 10,10-difluorodecyl alcohol ethoxylated with an average of 4 moles of ethylene oxide (0.45 OH equivalents) is mixed with 385 grams of toluene and 54 grams of 50% aq. NaOH (0.675 equivalents). The water is removed by azeotropic distillation and when a moisture level of less than 0.8% is reached, about 46 grams (0.51 equivalents) of epichlorohydrin are slowly added. This mixture is allowed to react at 100°–110° C. for 24 hours. This mixture is removed and filtered to remove the NaCl and vacuum stripped to remove the toluene to give a liquid product.

EXAMPLE 3

Preparation of the Reaction Product of 2,2,2-trifluoroethyl alcohol•4EO and epichlorohydrin:

About 124 grams of trifluoroethyl alcohol ethoxylated with an average of 4 moles of ethylene oxide (0.45 OH equivalents) is mixed with 385 grams of toluene and 54 grams of 50% aq. NaOH (0.675 equivalents). The water is removed by azeotropic distillation and when a moisture level of less than 0.8% is reached, about 46 grams (0.51 equivalents) of epichlorohydrin are slowly added. This mixture is allowed to react at 100°–110° C. for 24 hours. This mixture is removed and filtered to remove the NaCl and vacuum stripped to remove the toluene to give a liquid reaction product.

EXAMPLE 4

Preparation of the Reaction Product of trifluorophenol•4EO and epichlorohydrin:

About 146 grams of trifluorophenol ethoxylated with an average of 4 moles of ethylene oxide (0.45 OH equivalents) is mixed with 385 grams of toluene and 54 grams of 50% aq. NaOH (0.675 equivalents). The water is removed by azeotropic distillation and when a moisture level of less than 0.8% is reached, about 46 grams (0.51 equivalents) of epichlorohydrin are slowly added. This mixture is allowed to react at 100°–110° C. for 24 hours. This mixture is removed and filtered to remove the NaCl and vacuum stripped to remove the toluene to give a liquid product.

EXAMPLE 5

An exterior acrylic latex flat water-based house paint is prepared from the following components:

| Raw material ingedients | Weight, kg |
| --- | --- |
| Grind portion | |
| water | 144.1 |
| propylene glycol | 72.3 |
| in-can preservative | 2.0 |
| cellulose thickener, 100% | 3.6 |
| dispersant, 25% | 14.7 |
| reaction product of Example 1 | 2.4 |
| defoamer | 2.4 |
| titanium dioxide | 210.8 |
| zinc oxide | 30.1 |
| extenders | 192.8 |
| Let-down portion | |
| latex emulsion, 53.3% | 391.0 |
| polymeric opacifier | 79.5 |
| texanol | 11.9 |
| defoamer | 2.4 |
| mildewcide | 2.4 |
| polyurethane thickener, 25% | 12.0 |
| aqueous ammonia, 28% | 2.7 |
| water | 150.4 |
| Total | 1327.5 |

The above latex paint is free from foam and can be readily applied to wood siding, stucco, plasterboard, and other surfaces in and around a home to produce a smooth even coating.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A reaction product prepared by a process comprising reacting:

A) at least one compound having the general formula I:

$$R^1(X)_3 \qquad (I)$$

wherein each X group independently represents a halogen atom or one X group represents a halogen atom and two X groups represent an epoxy oxygen atom, which is attached to two adjacent carbon atoms in the $R^1$ group to form an epoxy group, and $R^1$ is an alkanetriyl group having from 3 to 10 carbon atoms; and B) at least one compound having the general formula II $$R^2X(AO)_nY \quad (II)$$

wherein $R^2$ represents a polyfluorinated organic group having from 1 to 36 carbon atoms and at least two fluorine atoms; X represents —O—, —S—, or $NR^3$— where $R^3$ is hydrogen or a $C_1$–$C_{18}$ alkyl group; each AO group is independently an ethyleneoxy, 1,2-propyleneoxy, or 1,2-butyleneoxy group, n is a number of from 1 to 200; and Y represents hydrogen, a mercapto group, an amino group or a $C_1$–$C_6$ alkylamino group in place of a terminal —OH group, with the proviso that when Y is a mercapto, amino, or a $C_1$–$C_6$ alkylamino group, n is at least 1.

2. The reaction product according to claim 1, wherein $R^2$ represents a polyfluorinated organic group having from 1 to 36 carbon atoms and at least 3 fluorine atoms.

3. The reaction product according to claim 1, wherein $R^2$ represents a fully fluorinated organic group having from 1 to 3 carbon atoms.

4. The reaction product according to claim 1, wherein component A) and component B) are reacted in a mole ratio of from about 0.1:1 to about 5:1.

5. The reaction product according to claim 1, wherein component A) and component B) are reacted in a mole ratio of from about 0.6:1 to about 2:1.

6. The reaction product according to claim 1, wherein component A) and component B) are reacted in a mole ratio of from about 0.8:1 to about 2:1.

7. The reaction product according to claim 1, wherein component A) and component B) are reacted in a mole ratio of from about 1.0:1 to about 1.5:1.

8. The reaction product according to claim 1, wherein component A) comprises epichlorohydrin.

9. The reaction product according to claim 1, wherein n represents a number of from 1 to about 100.

10. The reaction product according to claim 1, wherein n represents a number of from 2 to about 20.

11. The reaction product according to claim 1, wherein $R^2$ represents a straight or branched chain polyfluorinated alkyl group.

12. The reaction product according to claim 11, wherein n represents a number of from 1 to about 100.

13. The reaction product according to claim 1, wherein component B) comprises a compound of the general formula (IIa):

$$R^2O(EO)_m(PO)_p(BO)_qH \quad (IIa)$$

wherein $R^2$ represents a polyfluorinated organic group having from 1 to 36 carbon atoms and at least two fluorine atoms, m represents a number of from 0 to 100, p represents a number of from 0 to 50 wherein at least one of m, p or q is at least one and q represents a number of from 0 to 50.

14. The reaction product according to claim 13, wherein m represents a number of from 2 to about 20.

15. The reaction product according to claim 13, wherein component A) comprises epichlorohydrin.

16. The reaction product according to claim 13, wherein $R^2$ is a straight or branched polyfluorinated alkyl group having from 1 to 3 carbon atoms, m is a number of from 2 to 20, and p and q=0.

17. The reaction product according to claim 16, wherein component A) comprises epichlorohydrin.

18. A liquid composition comprising a defoaming-effective quantity of the reaction product according to claim 1.

19. The composition according to claim 18, wherein the liquid composition is a paint, a latex composition, an adhesive composition, an enamel, a lacquer, a baking finish, a coating composition containing a resin, a polyurethane coating, an organic finish remover, a drying oil, or a varnish.

* * * * *